United States Patent
Chen

(10) Patent No.: US 11,752,171 B2
(45) Date of Patent: Sep. 12, 2023

(54) USES OF INDUCED NEURAL STEM CELLS DERIVED FROM PERIPHERAL BLOOD MONONUCLEAR CELLS

(71) Applicant: Xuanwu Hospital Capital Medical University, Beijing (CN)

(72) Inventor: Zhiguo Chen, Beijing (CN)

(73) Assignee: WISEHEART MEDICAL VALLEY CO., LTD., Beijing (CN)

( * ) Notice: Subject to any disclaimer, the term of this patent is extended or adjusted under 35 U.S.C. 154(b) by 514 days.

(21) Appl. No.: 16/388,924

(22) Filed: Apr. 19, 2019

(65) Prior Publication Data
US 2019/0321399 A1    Oct. 24, 2019

(30) Foreign Application Priority Data
Apr. 24, 2018 (CN) .......................... 201810372724.7

(51) Int. Cl.
| | |
|---|---|
| C12N 5/00 | (2006.01) |
| C12N 5/02 | (2006.01) |
| A61K 35/15 | (2015.01) |
| A61P 25/28 | (2006.01) |
| A61K 35/30 | (2015.01) |
| C12N 5/0793 | (2010.01) |
| C12N 5/0735 | (2010.01) |
| C12N 15/86 | (2006.01) |
| C12N 5/074 | (2010.01) |

(52) U.S. Cl.
CPC .............. *A61K 35/15* (2013.01); *A61K 35/30* (2013.01); *A61P 25/28* (2018.01); *C12N 5/0018* (2013.01); *C12N 5/0606* (2013.01); *C12N 5/0619* (2013.01); *C12N 5/0696* (2013.01); *C12N 15/86* (2013.01); *C12N 2501/01* (2013.01); *C12N 2501/13* (2013.01); *C12N 2501/15* (2013.01); *C12N 2760/18843* (2013.01)

(58) Field of Classification Search
CPC ................ C12N 5/0618; C12N 5/0619; C12N 2506/00; C12N 2506/115; A61K 35/15; A61P 25/28
See application file for complete search history.

(56) References Cited

FOREIGN PATENT DOCUMENTS

| | | |
|---|---|---|
| CN | 105219729 A | 1/2016 |
| WO | 02069975 A1 | 9/2002 |

OTHER PUBLICATIONS

Romito et al., 2016, Hindawi Publishing Corporation, Stem Cell International, vol. 2016, Article ID 9451492, p. 1-20.*
Paes et al., 2017, Cell Biology and Toxicology, vol. 33, No. 3, pp. 233-250.*
Kim et al., 2014, IOVS, vol. 55, No. 8, p. 5099-5108.*
Stern-Straeter et al., 2014, International Journal of Molecular Medicine, vol. 33, p. 160-170.*
Dib et al., 2011, J. of Cardiovasc. Trans. Res., 4:177-181.*
Wu et al., 2012, Aging Research reviews, vol. 11, p. 32-40.*
Agrahari et al., 2017, Expert Opinion on Drug Delivery, vol. 14, No. 10, p. 1145-1162.*
Ikonomou et al., 2017, Am J Respir Crit Care Med, vol. 195, p. 13-14.*
Ikehara et al., 2013, Frontier in Cell and Developmental Biology, vol. 1, Article 2, p. 1-2.*
Cooper et al., 2015, International Journal of Surgery, vol. 23, p. 211-216.*
Liu et al., 2017, Frontiers in Immunology, vol. 8, article 645, p. 1-6.*
Kleiveland, Charlotte, 2015, The Impact of Food Bioactives on Health: In Vitro and Ex Vivo Models, Chapter 15: Peripheral Blood Mononuclear Cells, Springer Open, European Cooperation in Science and Technology, pp. 161-167.*
Xihe Tang,Shuyan Wang,Yunfei Bai,Jianyu Wu,Linlin Fu,Mo Li,Qunyuan Xu,Zhi-Qing David Xu,Y.AIex Zhang,Zhiguo Chen; Conversion of adult human peripheral blood mononuclear cells into induced neural stem cell by using episomal vectors; «Stem Cell Research» vol. 16, Issue 2, Mar. 2016, pp. 236-242.
J Lu,H Liu,CL Huang,H Chen,Z Du,Y Liu,M Sherafat,SC Zhang; Generation of Integration-free and Region-Specific Neural Progenitors from Primate Fibroblasts; «Cell Rep.» vol. 3, Issue 5, May 30, 2013, pp. 1580-1591.
SN Dowey,X Huang,BK Chou,Z Ye,L Cheng; Generation of integration-free human induced pluripotent stem cells from postnatal blood mononuclear cells by plasmid vector expression; «Nat Protoc.» vol. 7, pp. 2013-2021 (2012).

* cited by examiner

*Primary Examiner* — Shin Lin Chen

(57) ABSTRACT

A method of treating neurodegenerative diseases or disorders, especially Parkinson's disease and a method of inducing neural stem cells from peripheral blood mononuclear cells. The induced neural stem cells can express neural stem cell-related genes and differentiate into neurons, astrocytes and oligodendrocytes. The dopaminergic precursors derived from the induced neural stem cells are transplanted into the striatum of the PD mouse models without any sign of tumorigenesis, thereby improving the behaviors of the PD mouse models and slowing down the progression of Parkinson's disease.

4 Claims, 16 Drawing Sheets

USES OF INDUCED NEURAL STEM CELLS DERIVED FROM PERIPHERAL BLOOD MONONUCLEAR CELLS

CROSS-REFERENCE TO RELATED APPLICATIONS

This application claims the benefit of priority from Chinese Patent Application No. CN201810372724.7, filed on Apr. 24, 2018. The content of the aforementioned application, including any intervening amendments thereto, is incorporated herein by reference in its entirety.

TECHNICAL FIELD

The application relates to biomedicine and neural stem cells, and specifically to a method of inducing neural stem cells with non-integrative heat-inactivated Sendai virus vectors and uses of the induced neural stem cells (iNSCs), especially dopaminergic precursors (DA precursors) differentiated from the iNSCs in the cell transplant treatment for Parkinson's disease.

BACKGROUND

Stem cell transplant makes it possible to treat many neurological diseases or disorders, such as Parkinson's disease, amyotrophic lateral sclerosis (ALS), traumatic brain and spinal cord injury. It has been demonstrated that embryonic stem cell-derived neural stem cells can be used to treat these diseases to some extent, but their applications are limited due to tumorigenesis of embryonic stem cells, immune rejection of allograft and ethical controversy. The induced pluripotent stem cells (iPSCs) derived from human fibroblasts are differentiated into neural stem cells for transplantation to treat neurologic disorders. However, it has been found that there are still many problems in the clinical treatment with iPSCs, such as tumorigenesis, low differentiation efficiency and safety problem. Recently, somatic cells are directly reprogrammed into induced neural stem cells (iNSCs) without undergoing a stage of iPSCs resulting in reduced tumorigenesis and increased differentiation efficiency, which has become a focus in the research of stem cells.

In the research of induced neural stem cells (iNSCs), ring et al. used retroviral vectors carrying Sox2 to transduce human fibroblasts, and neural stem cell clones appeared after 6-10 days. However, the retroviral gene sequence can be integrated into the host cell's gene sequence, leading to mutations in the host cell's gene. Duanqing Pei et al. used non-integrative plasmid vectors oriP/EBNA carrying Oct4, Sox2, Sv40LT, Klf4 and microRNA302-367 to electrotransduce living cells from human urine to produce neural stem cells capable of expressing Sox1,Sox2, Pax6. These iNSCs differentiate into astrocytes and dopaminergic neurons. Suchun Zhang et al. used Sendai viruses carrying exogenous Oct4, Sox2, Klf4, and c-Myc genes to transduce human fibroblasts to produce transduced fibroblasts which were then cultured in a medium containing LIF, SB431541 and CHIR99021. Neural stem cell clones appeared after 13 days of culture, and these iNSCs can differentiate into neurons, astrocytes and oligodendrocytes. However, obtaining fibroblasts from human is traumatic, and the fibroblasts need to be cultured in vitro for a long period of time before transduction. In addition, fibroblasts derived from elderly patients are not easily transduced.

Therefore, there are several defects in the prior art in which a viral vector or a plasmid vector is used to induce human fibroblasts or cells from human urine. For example, a traumatic injury may occur during the process of obtaining fibroblasts, and it is also difficult to culture fibroblasts in vitro; the source of cells is prone to contamination, for example, during collecting cells from urine, especially in a ward; and integrative viral vectors may cause a genetic mutation in the host cells.

During the past 20 years, cell therapy for Parkinson's disease has attracted attention from health care workers and biologists, but there is no report on the transplantation treatment with DA precursors differentiated from the induced neural stem cells.

SUMMARY

An object of this application is to provide a process for inducing peripheral blood mononuclear cells (PBMNCs) into neural stem cells using a non-integrative vector, and differentiating the neural stem cells into dopaminergic precursors to treat Parkinson's disease, such that behaviors of the Parkinson's disease (PD) animal models are improved, which enables cell transplantion treatment for Parkinson's disease.

In a first aspect, the present invention provides a method of treating Parkinson's disease in a subject, including:
  a) inducing neural stem cells (NSCs);
  b) selecting and differentiating the induced neural stem cells (iNSCs) into dopaminergic precursors; and
  c) administering the differentiated dopaminergic precursors into striatum of the subject thereby treating the Parkinson's disease.

In an embodiment, step a includes:
  (i) extracting mononuclear cells from peripheral blood to obtain peripheral blood mononuclear cells (PBMNCs) and expanding the PBMNCs in a medium;
  (ii) transducing the expanded PBMNCs with a Sendai viral vector carrying OCT4, SOX2, c-MYC and KLF-4 genes;
  (iii) seeding the transduced PBMNCs onto a Matrigel-coated plate followed by culturing in a medium until neural stem cell clones appear; and
  (iv) transferring the neural stem cell clones for neural stem cell expansion in which the neural stem cells are subjected to a high-temperature culture to obtain Sendai virus-inactivated neural stem cells.

In an embodiment, step b comprises the following steps:
  1) culturing the neural stem cells obtained in step iv) in a medium comprising a basic medium consisting of DMEM/F12, 1×N2, 1×B27, 1% of GlutaMAX and 1% of NEAA; SAG1 and FGF8 for 10 days; and optionally,
  2) after 10 days of culture in step 1), transferring the neural stem cells to a medium comprising a basic medium consisting of DMEM/F12, 1×N2, 1×B27, 1% of GlutaMAX and 1% of NEAA; BDNF, GDNF, AA, DAPT, cAMP and TGF-β III and then culturing the neural stem cells for two weeks to obtain the dopaminergic precursors.

In an embodiment, in step i), by using Ficoll density gradient centrifugation, an intermediate cloudlike layer comprising CD34+ hematopoietic stem cells and PBMNCs comprising lymphocytes and monocytes is obtained.

In an embodiment, in step i), the step of "extracting mononuclear cells from peripheral blood" comprises: sampling blood intravenously and diluting the blood with PBS; collecting mononuclear cells by density gradient centrifugation and transferring the obtained intermediate cloudlike layer to a centrifuge tube and adding PBS followed by centrifugation; removing a supernatant and resuspending the cells with PBS; repeating the centrifugation twice, preferably, at 4° C. for 10 minutes; removing the supernatant and resuspending the cells with PBS for counting.

In an embodiment, the high-temperature culture is carried out at 38.5-39.5° C., preferably, 39° C. for one week to one month. The specific time period for culture depends on the inactivation of Sendai viral vectors. After the high-temperature culture, PCR assay is used to determine whether the exogenous genes and vector genes are present in the transduced stem cells.

In an embodiment, in step i), the medium for expanding the PBMNCs comprises a basic medium consisting of 48.96-48.97% of Iscove's modified Dulbecco's medium (IMDM), 48% of Ham's F-12, 1% of insulin-transferrin-selenium, 1% of chemically defined concentration concentrate, 1% of L-glutamine, 0.05 mg/ml of L-vitamin C, 5 mg/ml of bovine serum albumin (BSA) and 0.018 μL/mL of thioglycerol; 100 ng/mL of recombinant human stem cell factor; 10 ng/mL of recombinant human interleukin 3; 2 U/mL of erythropoietin; 40 ng/mL of insulin-like growth factor IGF-1; 1 μM of dexamethasone; and 100 μg/mL of human transferrin.

In an embodiment, in step iii), the medium for culturing comprises a basic medium consisting of DMEM/F12 and 1×N2, neurobasal and 1×B27, 1% of GlutaMAX and 1% of NEAA; 10 ng/mL of recombinant human leukemia inhibitory factor (rhLIF); CHIR99021 and SB431542.

In an embodiment, the differentiated neural stem cells in step 1) or in step 2) are administered into the striatum of the subject with Parkinson's disease.

In an embodiment, the expanded PBMNCs are predominantly erythroid progenitor cells.

In a second aspect, the application provides a method of treating a neurodegenerative disease or disorder in a subject, comprising:
 a) inducing neural stem cells (NSCs);
 b) selecting and differentiating the induced neural stem cells (iNSCs) into a neuronal precursor corresponding to the neurodegenerative disease or disorder; and
 c) administering the neuronal precursor to the subject thereby treating the neurodegenerative disease;
 where the neurodegenerative disease or disorder is selected from the group consisting of Parkinson's disease, stroke, injury of cranial nerves, spinal cord injury and amyotrophic lateral sclerosis (ALS).

In an embodiment, step a comprises:
 i) extracting mononuclear cells from peripheral blood to obtain peripheral blood mononuclear cells (PBMNCs) and expanding the PBMNCs in a medium;
 ii) transducing the expanded PBMNCs with a Sendai viral vector carrying OCT4, SOX2, c-MYC and KLF-4 genes;
 iii) seeding the transduced PBMNCs onto a Matrigel-coated plate followed by culturing in a medium until neural stem cell clones appear; and
 iv) transferring the neural stem cell clones for neural stem cell expansion in which the neural stem cells are subjected to a high-temperature culture to obtain Sendai virus-inactivated neural stem cells.

In an embodiment, the induced neural stem cells is capable of expressing neural stem cell-related genes, and differentiating into different kinds of neurons comprising dopaminergic neurons, and different kinds of glial cells.

In a third aspect, the application provides a method of producing dopaminergic precursors, comprising:
 a) inducing neural stem cells (NSCs) by a method comprising:
  i) extracting mononuclear cells from peripheral blood to obtain peripheral blood mononuclear cells (PBMNCs) and expanding the PBMNCs in a medium;
  ii) transducing the expanded PBMNCs with a Sendai viral vector carrying OCT4, SOX2, c-MYC and KLF-4 genes;
  iii) seeding the transduced PBMNCs onto a Matrigel-coated plate followed by culturing in a medium until neural stem cell clones appear; and
  iv) transferring the neural stem cell clones for neural stem cell expansion in which the neural stem cells are subjected to a high-temperature culture to obtain Sendai virus-inactivated neural stem cells; and
 b) selecting and differentiating the induced neural stem cells (iNSCs) into dopaminergic precursors by a method comprising:
  1) culturing the neural stem cells obtained in step iv) in a medium comprising a basic medium consisting of DMEM/F12, 1×N2, 1×B27, 1% of GlutaMAX and 1% of NEAA; SAG1 and FGF8 for 10 days; and optionally
  2) after 10 days of culture in step 1), transferring the neural stem cells to a medium comprising a basic medium consisting of DMEM/F12, 1×N2, 1×B27, 1% of GlutaMAX and 1% of NEAA; BDNF, GDNF, AA, DAPT, cAMP and TGF-β III and then culturing the neural stem cells for 2 weeks to produce the dopaminergic precursors.

In an embodiment, in step iv), the high-temperature culture is carried out at 38.5-39.5° C., preferably at 39° C. for one week to one month. The specific time priod for culture depends on the inactivation of Sendai viral vectors.

In an embodiment, in step i), the medium for expanding the PBMNCs comprises a basic medium consisting of 48.96-48.97% of Iscove's modified Dulbecco's medium (IMDM), 48% of Ham's F-12, 1% of insulin-transferrin-selenium, 1% of chemically defined concentration concentrate, 1% of L-glutamine, 0.05 mg/ml of L-vitamin C, 5 mg/ml of bovine serum albumin (BSA) and 0.018 μL/mL of thioglycerol; 100 ng/mL of recombinant human stem cell factor; 10 ng/mL of recombinant human interleukin 3; 2 U/mL of erythropoietin; 40 ng/mL of insulin-like growth factor IGF-1; 1 μM of dexamethasone; and 100 μg/mL of human transferrin.

In an embodiment, in step iii), the medium for culturing comprises a basic medium consisting of DMEM/F12 and 1×N2, neurobasal and 1×B27, 1% of GlutaMAX and 1% of NEAA; 10 ng/mL of recombinant human leukemia inhibitory factor (rhLIF), CHIR99021 and SB431542.

It should be understood that various technical features described above and various technical features specifically described hereinafter (for example, in embodiments) of the present invention can be combined with each other to constitute a new or preferred technical solution that will not be described here due to space of this application.

The application provides the following advantages.

1. The neural stem cells are induced from peripheral blood using non-integrative Sendai viral vectors. The vectors can be inactivated under the elevated temperature by which the neural stem cells are not affected, thereby maintaining their characteristics and stability. The Sendai viral vector used herein is a single-stranded RNA viral vector which is transduced into the cytoplasm of neural stem cells and is not integrated into the genome of neural stem cells. In addition, the viral vector may be inactivated at 39° C. Sendai virus has better non-integrative property, controllable induction and shortened induction time than the integrative viral vector and the non-integrative plasmid vector.

The iNSCs is capable of differentiating into dopaminergic neurons and various neurons and glial cells in vitro. In addition, the peripheral blood sampling is simple and minimally traumatic, which is less affected by operating conditions and thus is less susceptible to contamination.

2. The iNSCs can be passaged many times without tumorigenesis. The whole-genome sequencing results for neural stem cells demonstrate that harmful mutations of proto-oncogene, tumor suppressor gene and neural stem cell-related genes do not occur, and it is shown that the method is safe and effective.

3. The iNSCs, obtained by the method with a shortened process and a high efficiency, is able to differentiate into dopaminergic neurons in vitro and secrete dopamine.

4. The dopaminergic precursors are transplanted into the SCID PD mouse models, and the results show that cell transplantation is safe and effective in the treatment of Parkinson's disease in animal models.

DETAILED DESCRIPTION OF EMBODIMENTS

The present application will be further illustrated below with reference to the embodiments. It should be understood that these embodiments are merely illustrative of the invention and are not intended to limit the scope thereof.

EXAMPLE 1

Induction of Neural Stem Cells from Peripheral Blood Mononuclear Cells (PBMNCs)

Step 1: Isolation of PBMNCs (1) At room temperature, 6 mL of blood was collected from a peripheral vein of an adult to store in a heparin anticoagulant tube which was mixed upside down 5 times.

(2) Mononuclear cells were harvested by using Ficoll density gradient centrifugation. The peripheral blood was diluted with PBS in a ratio of 1:2, and stored in a 50 mL centrifuge tube at room temperature. If the volume of the diluted blood was less than 35 mL, PBS supplement was added.

(3) Another 50 mL centrifuge tube containing 15 mL of Ficoll-Paque Premium was tilted 45 degrees allowing for slow inflow of the diluted blood.

(4) The centrifuge tube was then centrifuged at 750×g and at 25° C. for 30 min.

Figure 1:
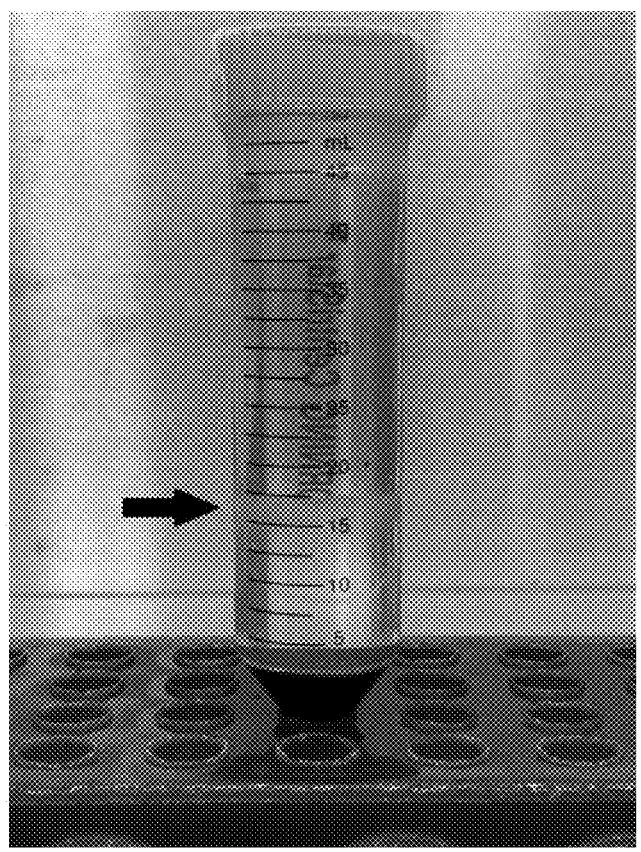
FIG. 1 shows an intermediate cloudlike layer after centrifugation of peripheral blood by using Ficoll density gradient centrifugation, where the arrow indicates the cloudlike mononuclear cell layer.

(5) After centrifugation, an upper layer in the centrifuge tube was plasmas, and an intermediate cloudlike layer was mononuclear cells of interest, as shown in FIG. 1.

(6) The upper layer was pipetted, and the cloudlike layer was transferred to a 50 mL centrifuge tube.

(7) The cloudlike layer was added with 30 mL of PBS and centrifuged at 350×g and at 4° C. for 10 min, during which the centrifuge was opened for braking.

(8) The supernatant was pipetted, and the cells were resuspended with 25 mL of PBS followed by centrifugation at 300×g and at 4° C. for 10 min.

(9) The supernatant was pipetted, and the cells were resuspended with 25 mL of PBS followed by centrifugation at 300×g and at 4° C. for 10 min (that is, step (8) was repeated).

(10) The supernatant was removed, and the cells were resuspended with 5 mL of PBS for counting.

Step 2: Expansion of PBMNCs (1) On day 14, the PBMNCs obtained by centrifugation were resuspended in a medium at $2 \times 10^6$–$3 \times 10^6$ cells/mL and incubated at 37° C. and 5% $CO_2$ for 2 days.

(2) On day 11, the cells were collected and centrifuged at 200×g. The supernatant was discarded, and the cells were then resuspended in a medium at $1 \times 10^6$ cells/mL and incubated in an incubator for 3 days.

(3) On day 8, the cells were collected and centrifuged at 200×g. The supernatant was discarded, and the cells were then resuspended in a medium at $1 \times 10^6$ cells/mL and incubated in an incubator for 4 days.

(4) On day 4, the cells were collected and centrifuged at 200×g. The supernatant was discarded, and the cells were then resuspended in a medium at $1 \times 10^6$ cells/mL and incubated in an incubator for 4 days.

Figure 2:
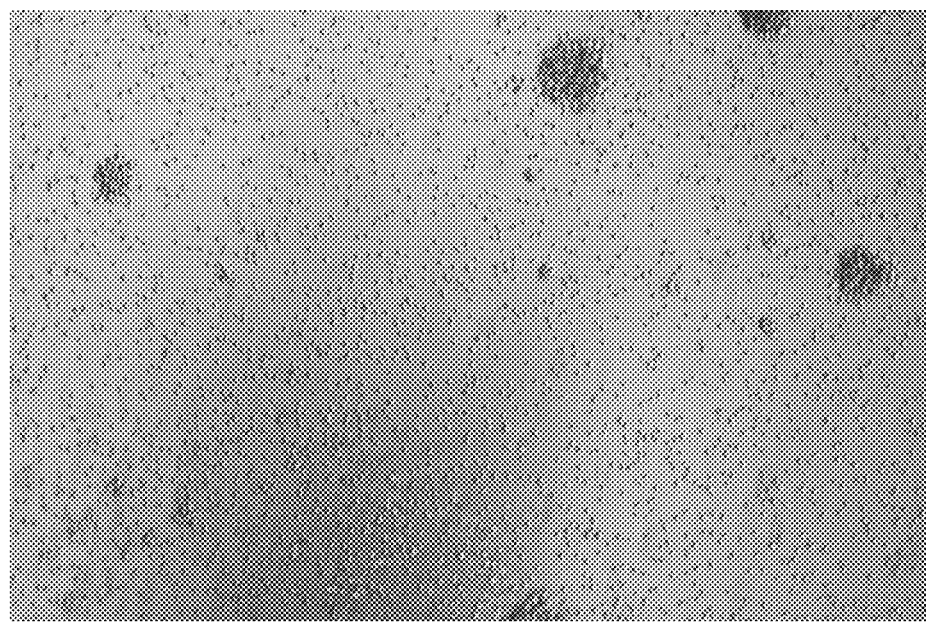
FIG. 2 shows morphology of peripheral blood mononuclear cells after 14 days of in vitro expansion.
Figure 3:
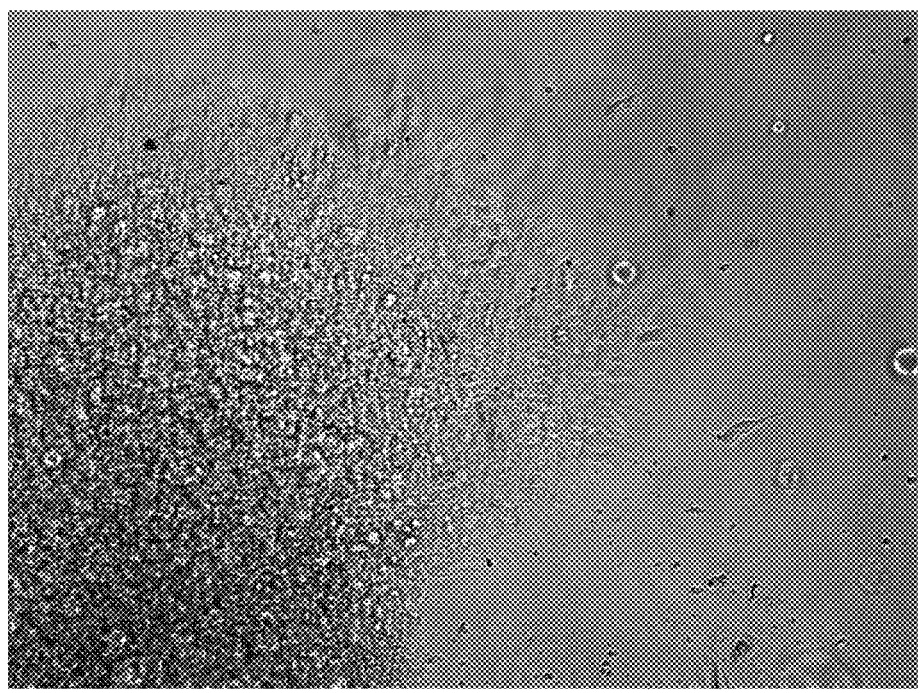
FIG. 3 shows the emergence of neural stem cell clones after peripheral blood mononuclear cells are expanded in vitro for 2 weeks and then transducted with Sendai viral vectors for 10 days.

Step 3: Transduction (1) On day 0, the cells were collected, counted and centrifuged. The supernatant was discarded and $2 \times 10^6$ PBMNCs were resuspended with 5 mL of PBS. The resuspension was centrifuged at 200×g and room temperature for 5 min and the supernatant was discarded. The cell morphology was shown in FIG. 2.

(2) The obtained cells were resuspended in 3 mL of a medium containing viruses for transduction.

(3) The incubation was performed at 37° C. and at 5% $CO_2$.

Step 4: Culture of NSCs (1) Preparation: 1 mL of Matrigel diluted with a medium in a ratio of 1:100 was placed in a 6-well plate and incubated overnight for future use.

(2) The PBMNCs was centrifuged 2 days after transduction, and the supernatant was discarded. The cells were resuspended in a medium and seeded into the 6-well plate at $(2-4) \times 10^5$/well. The medium was replaced every other day. On day 10 or so, stem cell clones appeared, and the medium was replaced to allow for continuous expansion of the cells.

Figure 4:
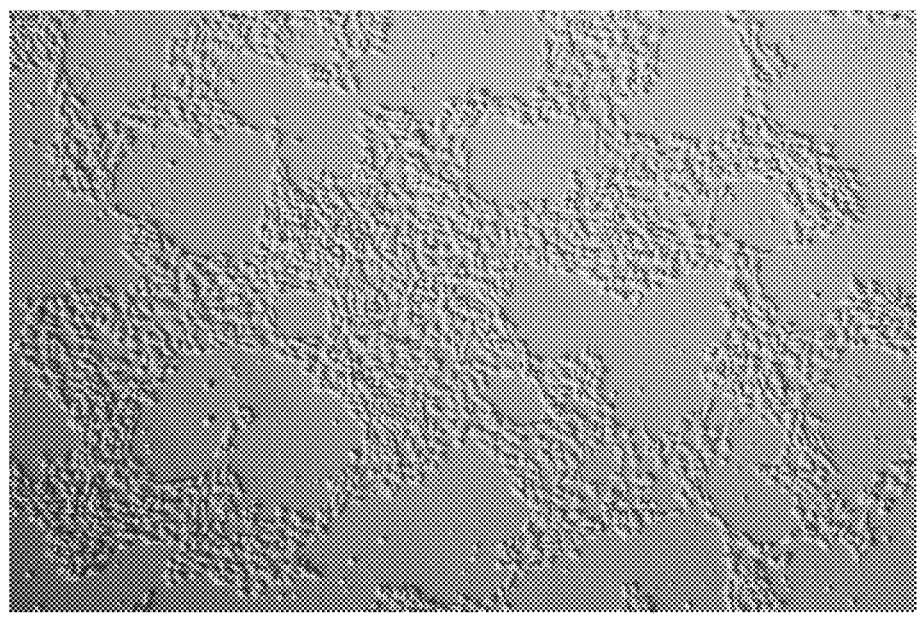
FIG. 4 shows morphology of neural stem cells during adherent culture, which is similar to that of neuroepithelial cells.

(3) On day 20 to day 30, the clones expanded and the cells were blown down using a pipette and transferred to a 96-well plate coated with PDL-Laminin for later expansion. As shown in FIG. 4, the induced neural stem cells had a morphology similar to that of the neural stem cells under light microscope.

(4) After one month of passage, the iNSCs were incubated at 39° C. for a week. Then PCR assay was then used to identify the iNSCs.

EXAMPLE 2

Expression of Neural Stem Cell Marker Protein by the Induced Neural Stem Cells $5 \times 10^4$ iNSCs were plated onto a 12 mm slide coated with poly-D-lysine and laminin, and stained after cultured in a medium for 48 h. The specific steps were described as follows.

(1) The medium was pipetted, and the cells were washed twice with PBS and added with 4% paraformaldehyde for immobilization for 10 minutes.

(2) The paraformaldehyde was removed and the cells were added with 1 mL of 0.3% PBST, which is repeated twice at an interval of 5 minutes.

(3) The cells were blocked by 3% donkey serum at room temperature for 1 h. After that, the cells were added with primary antibodies (prepared by adding antibodies such as Nestin (in a dilution of 1:500, mouse, BD bioscience) and Sox1 (in a dilution of 1:200, goat, BD bioscience) to 1% donkey serum in a certain ratio) and incubated at 4° C. overnight.

(4) The primary antibodies were pipetted, and the cells were added with corresponding secondary antibodies and placed at room temperature in the dark for 2 h. FITC-conjugated donkey anti-mouse corresponding to Nestin was prepared in a dilution of 1:200, and Cy3-conjugated donkey anti-goat corresponding to Sox1 and Sox2 was prepared in a dilution of 1:400.

(5) The secondary antibodies were pipetted, and the cells were washed with PBS three times and then added with DAPI (Sigma-Aldrich) prepared in a dilution of 1:1000 for incubation for 10 minutes.

Figure 5:
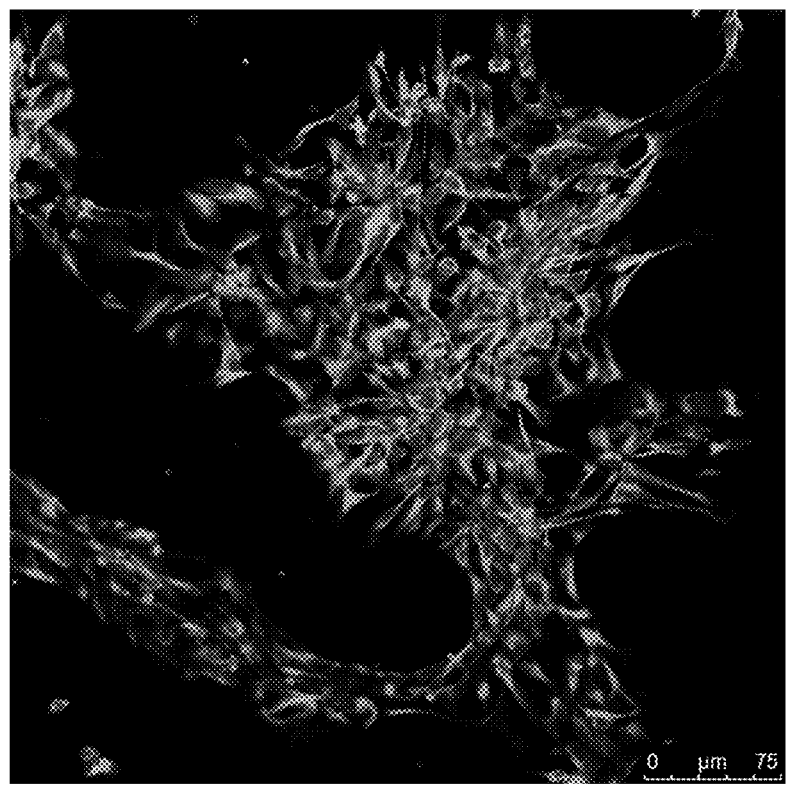
FIG. 5 shows identification of the expression of neural stem cell marker Nestin protein by induced neural stem cells using immunocytochemical staining, where green indicates Nestin protein and blue indicates DAPI cell nucleus.
Figure 6:
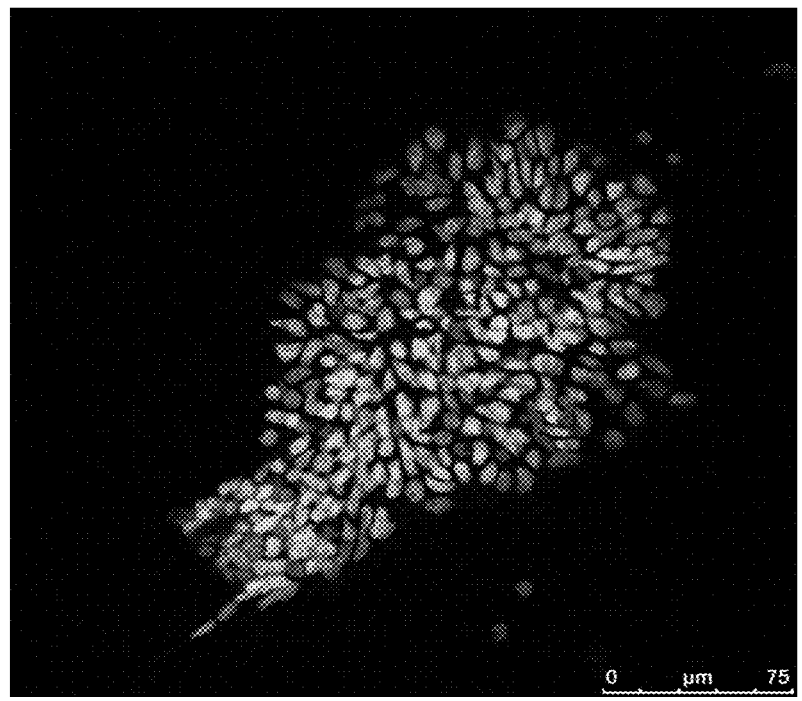
FIG. 6 shows identification of the expression of neural stem cell marker Pax6 protein by induced neural stem cells using immunocytochemical staining, where red indicates Pax6 protein and blue indicates DAPI cell nucleus.
Figure 7:
FIG. 7 shows identification of the expression of neural stem cell marker Sox1 protein by induced neural stem cells using immunocytochemical staining, where red indicates Sox1 protein and blue indicates DAPI cell nucleus.
Figure 8:
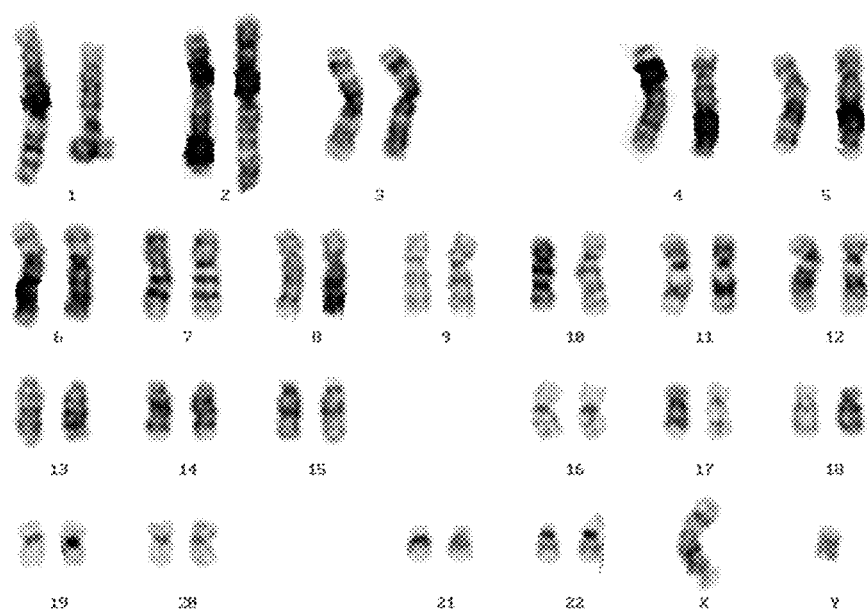
FIG. 8 shows the induced neural stem cells having a normal male karyotype (i.e., 46XY).

(6) The slide was mounted and then photographed by laser scanning confocal microscope. As shown in FIGS. 5, 6 and 7, the stem cells were found to express Nestin, Sox1, and Sox2 proteins. The iNSCs in the proliferative phase were lysed for karyotype analysis, and the results showed that the iNSCs had a normal karyotype (shown in FIG. 8).

EXAMPLE 3

Figure 9:
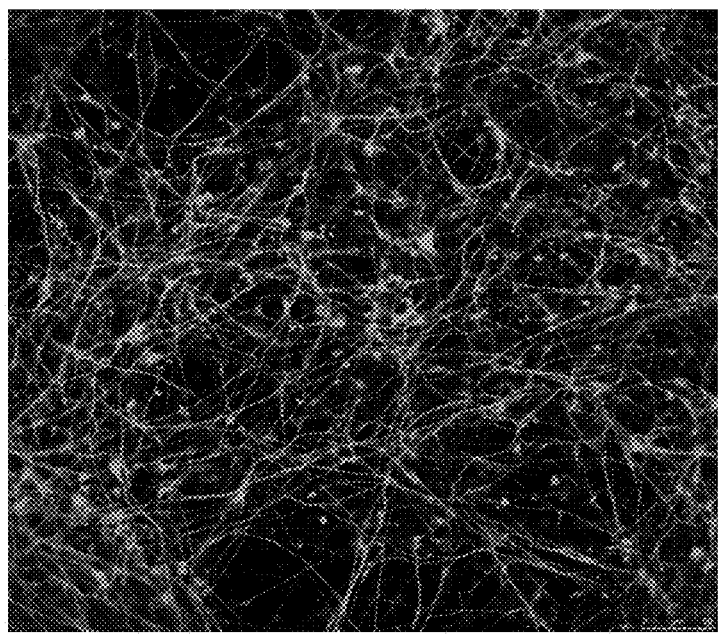
FIG. 9 shows identification of in vitro differentiation of induced neural stem cells into mature neurons using immunocytochemical staining, where green indicates TUJ1 protein and blue indicates DAPI cell nucleus.

Differentiation of Neural Stem Cells into Mature Neurons $2 \times 10^4$ iNSCs were plated onto a 12 mm slide coated with poly-D-lysine and laminin, and cultured in a medium for 24 h. After that, the medium was replaced with a medium for neuronal differentiation comprising DMEM: F12, 1% N2, 1% B27, 1% glutamine and 1% non-essential amino acid (NEAA, Life Technologies). The medium was replaced every other day, and the cells were immobilized after 6 weeks for immunocytochemical staining of MAP2 (in a dilution of 1:200, mouse, Sigma) and Neun (in a dilution of 1:400, rabbit, Millpore). The cells expressed mature neuronal proteins Map 2 and Neun, as shown in FIG. 9.

EXAMPLE 4

Figure 10:
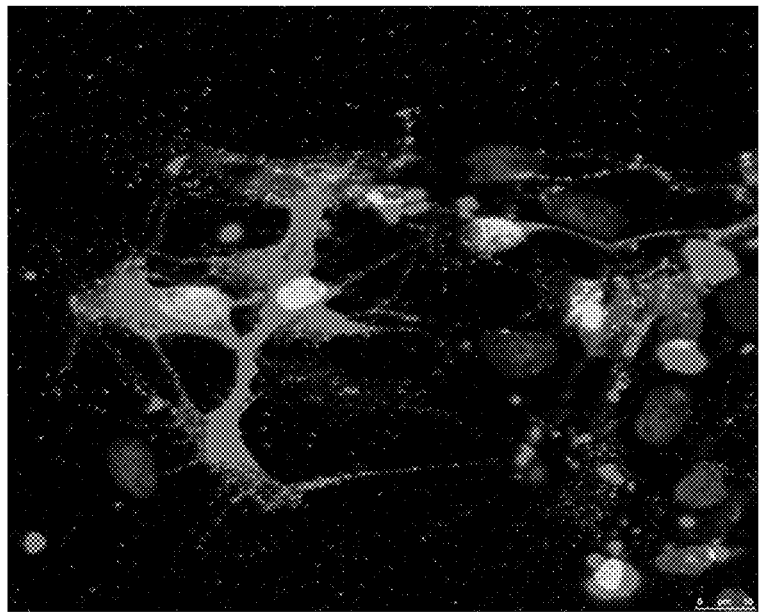
FIG. 10 shows identification of in vitro differentiation of induced neural stem cells into oligodendrocytes using immunocytochemical staining, where red indicates 04 protein and blue indicates DAPI cell nucleus.
Figure 13:
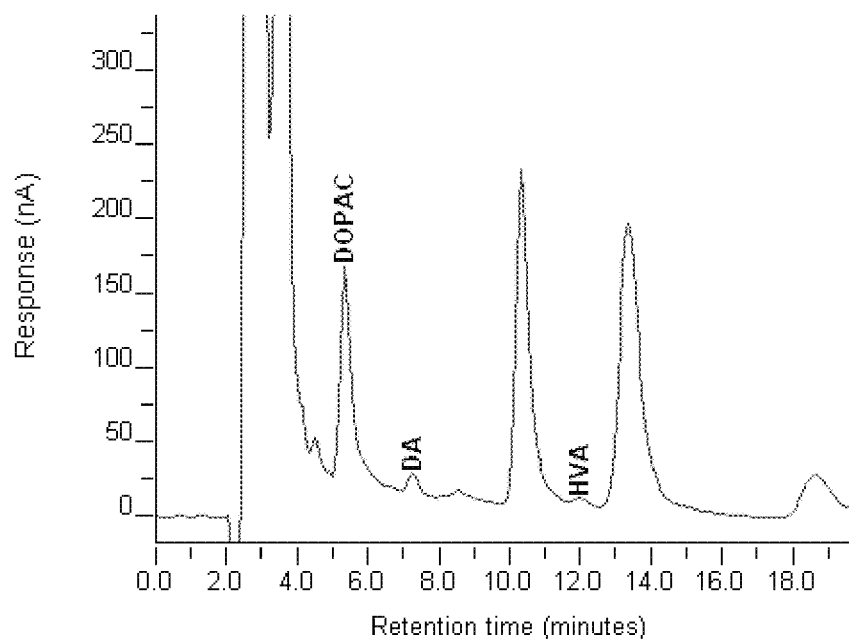
FIG. 13 is an HPLC curve for dopamine (DA), 3,4-dihydroxyphenylacetic acid (DOPAC) and homovanillic acid (HVA) secreted by dopaminergic neurons.
Figure 16:
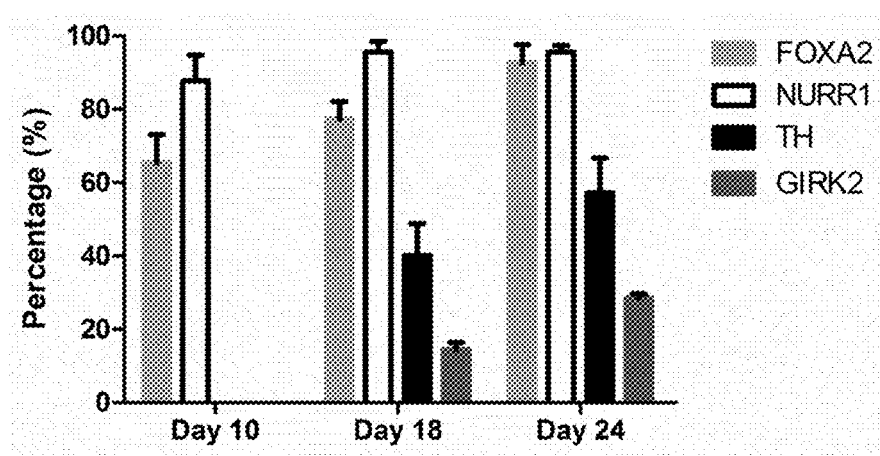
FIG. 16 shows expression ratio of different dopaminergic neuron markers on day 10, 18 and 24 of in vitro differentiation of induced neural stem cells. On day 24, the proportion of TH+ dopaminergic neurons reaches 57%, and the proportion of GIRK2+ cells is 28%, where GIRK2 is an A9 region-specific mature dopaminergic neuron marker.

Differentiation of Neural Stem Cells into Dopaminergic Neurons $2 \times 10^4$ iNSCs were plated onto a 12 mm slide coated with poly-D-lysine and laminin, and cultured in a medium for 24 h. After that, the medium was replaced with a basal medium for neuronal differentiation comprising DMEM: F12, 1% N2, 1% B27, 1% glutamine and 1% non-essential amino acid (NEAA). At the first stage, the basal medium was supplemented with chemical small molecules: 1 μM SAG1 (Enzo) and 100 ng/ml FGF8 (PeproTech). After 10 days of culture, the medium was replaced with a medium (prepared by adding BDNF, GDNF, AA, DAPT, cAMP and TGFβIII to the basal medium) for second stage. Then cellular immunochemical staining of TH (in a dilution of 1:500, Sheep, Mllpore) in the primary antibodies was performed after 2 weeks of culture. As shown in FIG. 10, the iNSCs were able to differentiate into TH+ dopaminergic neurons, where 42.51% of the TH+ cells also expressed A9 region-specific dopaminergic neuron marker GIRK2, indicating that the midbrain substantia nigra-specific dopaminergic neurons may be obtained in vitro in a fast and efficient manner. Statistical results of positive cells at different time points during differentiation were shown in FIG. 16. It can be seen that the method of the application can efficiently induce neural stem cells to differentiate into TH+ and midbrain substantia nigra-specific dopaminergic neurons. Determination of physiological secretion of dopaminergic neurons by HPLC was shown in FIG. 13.

EXAMPLE 5

Figure 11:
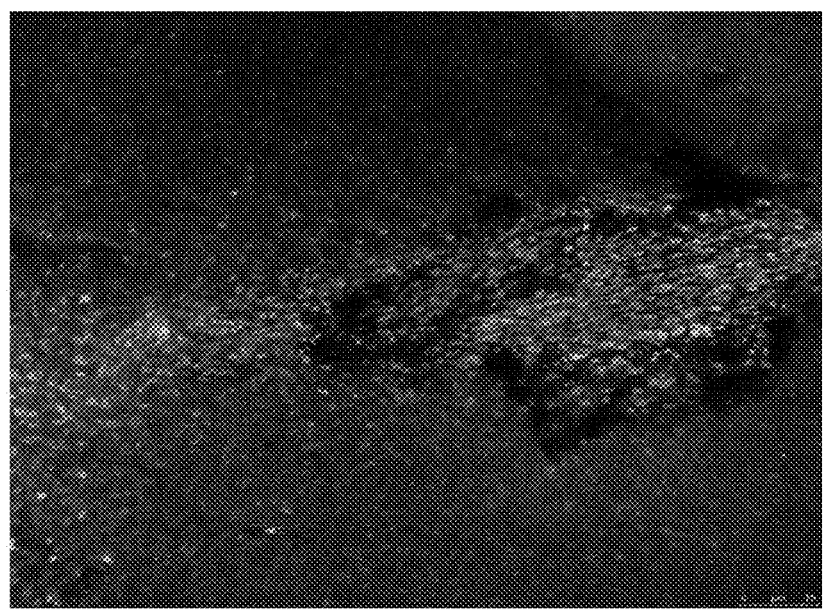
FIG. 11 shows identification results using immunohistochemical staining in which the induced neural stem cells in immunodeficient mice is capable of differentiation without tumorigenicity, where green indicates Nuclei protein; red indicates NeuN protein; and blue indicates DAPI cell nucleus.

Differentiation of Neural Stem Cells into Oligodendrocytes $2 \times 10^4$ iNSCs were plated onto a 12 mm slide coated with poly-D-lysine and laminin, and cultured in a medium for 24 h. After that, the medium was replaced with a basal medium for neuronal differentiation to which the following small molecules were added, including 1 μM trans-retinoic acid RA (Sigma-Aldrich), 20 ng PDGF-AB (PeproTech), 10 ng/mL bFGF (PeproTech) and SAG1 (Enzo). Two weeks later, the medium was replaced with another basal medium for neuronal differentiation to which the following small molecules were added, including 20 ng PDGF-AB (PeproTech), SAG1 (Enzo), 60 ng/mL thyroxine T3 (Sigma-Aldrich), 1 mM cyclic adenosine monophosphate (Sigma-Aldrich), 10 ng/mL insulin-like growth factor IGF-1 (PeproTech) and 10 ng/mL neurotrophic factor 3 NT3 (PeproTech). The cells were then subjected to cytochemical staining of O1 (in a dilution of 1:300, mouse, eBioscience) as the primary antibody. As shown in FIG. 11, the iNSCs differentiate into oligodendrocytes with O1 as a marker protein, scale bars: 50 μm.

EXAMPLE 6

In Vivo Differentiation of Neural Stem Cells without Tumorigenesis

Two neural stem cell lines derived from the same parental PBMNCs were selected for whole-genome sequencing to analyze the mutation between two daughter cells and parental cells by comparison. No mutation of the oncogene (that is, no tumorigenic risk) was found in the two daughter iNSCs.

Figure 12:
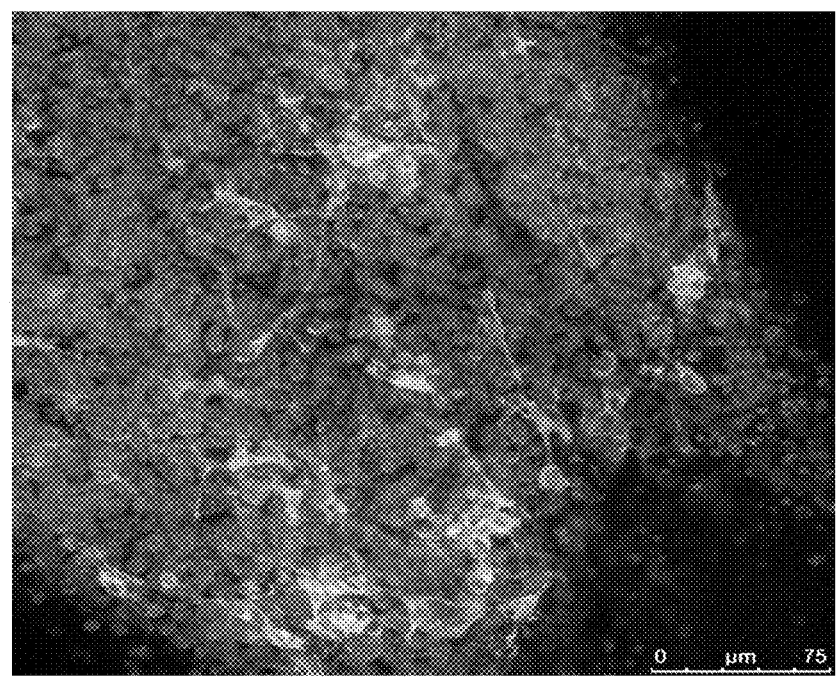
FIG. 12 shows identification of in vitro differentiation of neural stem cells into dopaminergic neurons using immunohistochemical staining, where red indicates TH protein and blue indicates DAPI cell nucleus.

The iNSCs were resuspended in 5% glucose solution at $1 \times 10^5/\mu L$. After the immunodeficient mice were anesthetized, the cell suspension was injected into the unilateral corpus striatum in the mouse by microsyringe under a stereotaxic condition. Two months later, the mice were perfused at general anesthesia, and the brain tissue was frozen-sliced and stained. It can be seen in FIG. 12 that the transplanted iNSCs can differentiate into Tuj-1 positive cells in mice.

EXAMPLE 7

Figure 14A:
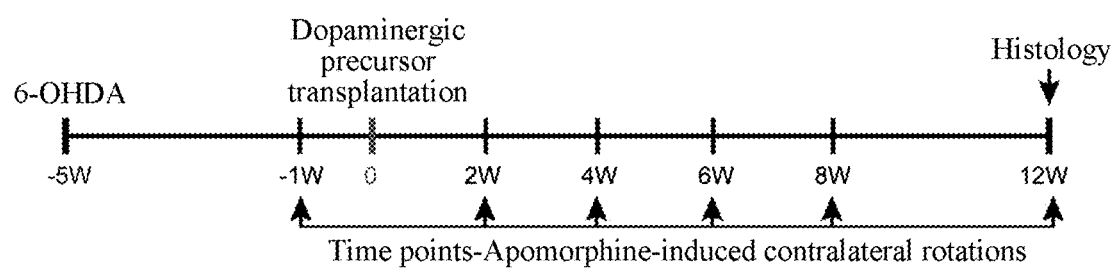
FIG. 14A is a flow chart showing PD immunodeficient mice modeling, cell transplantation and behavioral test.
Figure 14B:
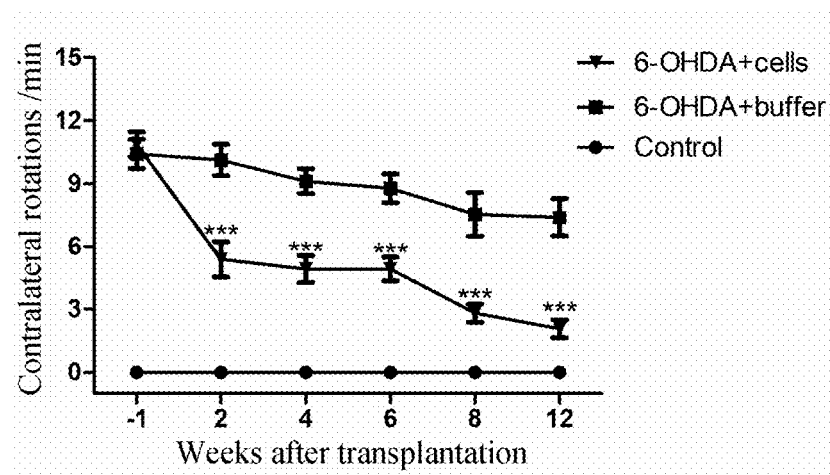
FIG. 14B shows the behavioral test results of PD mice, ***$p<0.001$.
Figure 15A:
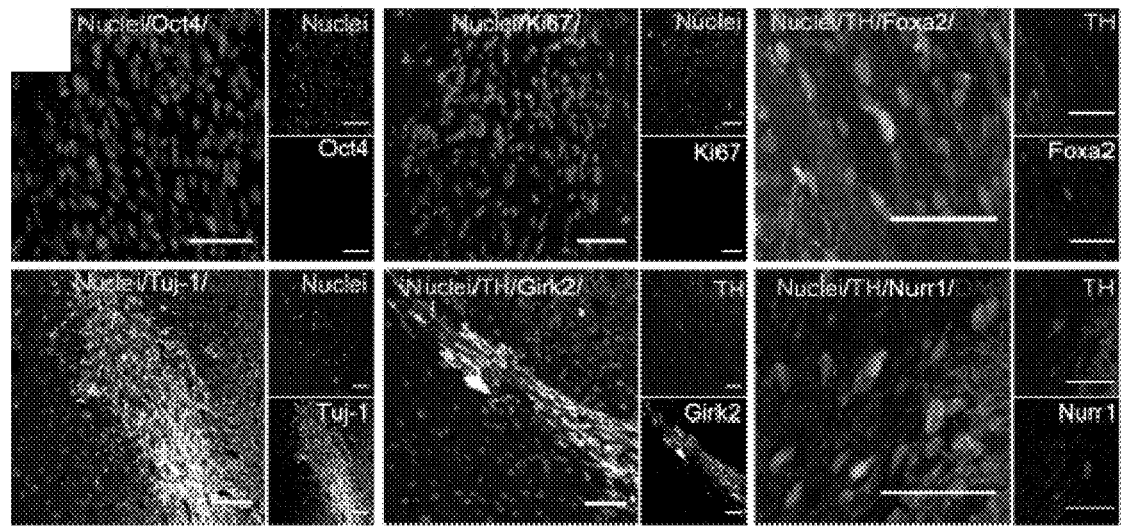
FIGS. 15A-B show histological staining results and statistical analysis for PD mouse cell transplantation group. (A): histological staining results for mice after cell transplantation. (B): statistical results of histological staining for the mouse cell transplantation group. It can be seen that the cells can differentiate into mature midbrain dopaminergic neurons, where TH+ cells account for 13.84%; a ratio of FOXA2 to TH is 86.78%; a ratio of NURR1 to TH is 91.72%; and a ratio of GIRK2 to TH is 98.77%.
Figure 15B:
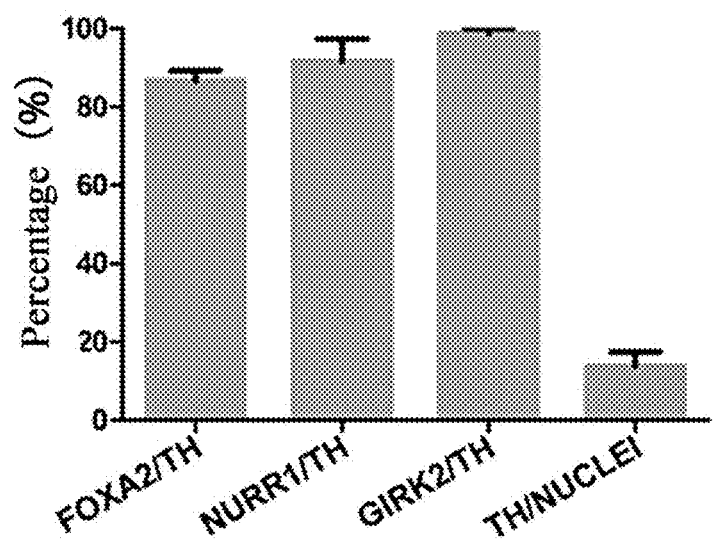

Transplantation of DA Precursors Differentiated from iNSCs into PD Mice with Significant Behavioral Difference $5 \times 10^3$ iNSCs were plated onto a 6-well plate coated with poly-D-lysine and laminin, and cultured in a medium for 24 h. After that, the medium was replaced with a medium I for neuronal differentiation comprising DMEM: F12, 1% N2, 1% B27, 1% glutamine, 1% non-essential amino acid (NEAA), SAG1 and FGF8. After 10 days of culture, the medium I was replaced with a medium II to which BDNF, GDNF, cAMP, AA (ascorbic acid), TGF-βIII and DAPT were supplemented for further 2 weeks of culture. The mice (SCID-beige) were lesioned unilaterally on the right side of the striatum by injecting 6-OHDA to generate PD models. $2 \times 10^5$ DA precursors including cells from day 10 and day 13 differentiation at a ratio of 1:7 were transplanted into the lesioned sites and the behavioral tests were performed 2, 4, 6, 8 and 12 weeks respectively after transplantation. Tumor development was not observed in the brain of PD mice in the engrafted group which showed significantly improved behavioral performance that is different from that of the buffer group (***$p<0.001$). As shown in FIG. 14, a flow chart including SCID-beige PD mouse modeling, cell transplantation and behavior testing was illustrated. The histological staining results indicated the differentiation of iNSCs into mature midbrain dopaminergic neurons, as shown in FIG. 15.

Unless otherwise specified, reagents used herein are commercially available.

Obviously, these embodiments are merely illustrative of the invention, and are not intended to limit the scope of the invention. Various forms of variations and modifications that are not described in detail here, may be made by those skilled in the art based on the above description, and obvious variations and modifications derived therefrom should fall within the scope of the invention.

What is claimed is:

1. A method of treating Parkinson's disease in a subject, comprising:
    a) inducing human peripheral blood mononuclear cells (PBMNCs) into neural stem cells (NSCs) by:
        i) expanding the PBMNCs in a first medium that comprises a basic medium consisting of 48.96-48.97% of Iscove's modified Dulbecco's medium (IMDM), 48% of Ham's F-12, 1% of insulin-transferrin-selenium, 1% of chemically defined lipid concentrate, 1% of L-glutamine, 0.05 mg/ml of L-vitamin C, 5 mg/ml of bovine serum albumin (BSA) and 0.018 μL/mL of thioglycerol; 100 ng/mL of recombinant human stem cell factor; 10 ng/mL of recombinant human interleukin 3; 2 U/mL of erythropoietin; 40 ng/mL of insulin-like growth factor 1 (IGF-1); 1 μM of dexamethasone, and 100 μg/mL of human transferrin;
        ii) transducing the expanded PBMNCs with a Sendai virus vector operable to carry OCT4, SOX2, c-MYC and KLF-4 genes;
        iii) culturing the transduced PBMNCs in a second medium that comprises a basic medium consisting of DMEM/F12 and 1×N2, neurobasal and 1×B27, 1% of GlutaMAX and 1% of non-essential amino acid (NEAA); 10 ng/mL of recombinant human leukemia inhibitory factor (rhLIF), CHIR99021 and SB431542 until neural stem cell clones appear; and
        iv) transferring the neural stem cell clones for neural stem cell expansion in which the neural stem cells are subjected to a high-temperature culture;
    b) differentiating the neural stem cells into dopaminergic precursors by:
        1) culturing the neural stem cells obtained in step iv) in a third medium that comprises a basic medium consisting of DMEM/F12, 1×N2, 1×B27, 1% of GlutaMAX and 1% of non-essential amino acids (NEAA); surface antigen 1 (SAG1) and fibroblast growth factor 8 (FGF8) for 10 days; and
        2) after 10 days of culture in step 1), transferring the neural stem cells to a fourth medium that comprises a basic medium consisting of DMEM/F12, 1×N2, 1×B27, 1% of GlutaMAX supplement and 1% of NEAA; brain-derived neurotrophic factor (BDNF), glial cell-derived neurotrophic factor (GDNF), ascorbic acid (AA), DAPT, cyclic adenosine monophosphate (cAMP) and transforming growth factor-β receptor type III (TGF-β III), and then culturing the neural stem cells for two weeks such that the dopaminergic precursors are obtained, wherein the dopaminergic precursors are capable of differentiation into human TH+ dopaminergic neurons expressing A9 region-specific dopaminergic neuron marker G protein-gated inwardly rectifying potassium channel (GIRK2) in vivo after transplantation; and c) administering the dopaminergic precursors obtained in step 2) into striatum of the subject by direct injection thereby treating the Parkinson's disease.

2. The method of claim 1, wherein in step i), by using Ficoll density gradient centrifugation, an intermediate cloudlike layer that comprises CD34+ hematopoietic stem cells and the PBMNCs comprising lymphocytes and monocytes is obtained.

3. The method of claim 1, wherein in step iv), the high-temperature culture is carried out at 38.5-39.5° C. for one week to one month until the Sendai virus vector is inactivated.

4. The method of claim 1, wherein the expanded PBMNCs is predominantly erythroid progenitor cells.

* * * * *